(12) United States Patent
Molloy et al.

(10) Patent No.: US 9,439,429 B2
(45) Date of Patent: Sep. 13, 2016

(54) SYNERGISTIC FUNGICIDAL COMPOSITION AND METHODS OF USE

(75) Inventors: Christopher Molloy, New Plymouth (NZ); Peter James Hayward, New Plymouth (NZ); Paul Garry Lobb, New Plymouth (NZ); George William Mason, New Plymouth (NZ); Stephen Millward, New Plymouth (NZ); Wallace James Rae, New Plymouth (NZ); André Frederik Siraa, New Plymouth (NZ)

(73) Assignee: ZELAM LIMITED, New Plymouth (NZ)

( * ) Notice: Subject to any disclaimer, the term of this patent is extended or adjusted under 35 U.S.C. 154(b) by 0 days.

(21) Appl. No.: 13/702,913

(22) PCT Filed: Jun. 22, 2011

(86) PCT No.: PCT/NZ2011/000119
§ 371 (c)(1),
(2), (4) Date: Dec. 7, 2012

(87) PCT Pub. No.: WO2012/002826
PCT Pub. Date: Jan. 5, 2012

(65) Prior Publication Data
US 2013/0090238 A1  Apr. 11, 2013

(30) Foreign Application Priority Data

Jun. 29, 2010 (NZ) .......................................... 586483
Jun. 15, 2011 (NZ) .......................................... 593471

(51) Int. Cl.
*A01N 43/653* (2006.01)

(52) U.S. Cl.
CPC .................................. *A01N 43/653* (2013.01)

(58) Field of Classification Search
CPC ........................ A01N 43/653; A01N 2300/00
See application file for complete search history.

(56) References Cited

U.S. PATENT DOCUMENTS

| 7,056,919 B2* | 6/2006 | Ross et al. ..................... 514/242 |
| 7,691,444 B2* | 4/2010 | Hayward et al. ........ 427/255.25 |
| 2004/0248973 A1 | 12/2004 | Ross et al. |
| 2006/0252847 A1* | 11/2006 | Hayward et al. ............. 523/122 |
| 2008/0190575 A1* | 8/2008 | Lu et al. ....................... 162/161 |

FOREIGN PATENT DOCUMENTS

| GB | 2438404 A | 11/2007 |
| WO | WO 2004/054766 A1 | 7/2004 |
| WO | WO 2004/067507 A2 | 8/2004 |
| WO | WO 2007135435 | 11/2007 |

OTHER PUBLICATIONS

International Search Report and Written Opinion for PCT Application PCT/NZ2011/000119; Dated Jun. 22, 2011.

\* cited by examiner

*Primary Examiner* — Sean Basquill
(74) *Attorney, Agent, or Firm* — Lucas & Mercanti, LLP

(57) ABSTRACT

Described is a broad spectrum, synergistic fungicidal composition when used for the preservation of a glued wood product comprising as active ingredients:
(A) triadimefon, and
(B) cyproconazole
characterized in that the weight ratio of (A):(B) is from about 20:1 to about 1:1, the composition being further characterized in that the application rate for the composition is from about 10 gai/m$^3$ to about 6,000 gai/m$^3$.

9 Claims, 1 Drawing Sheet

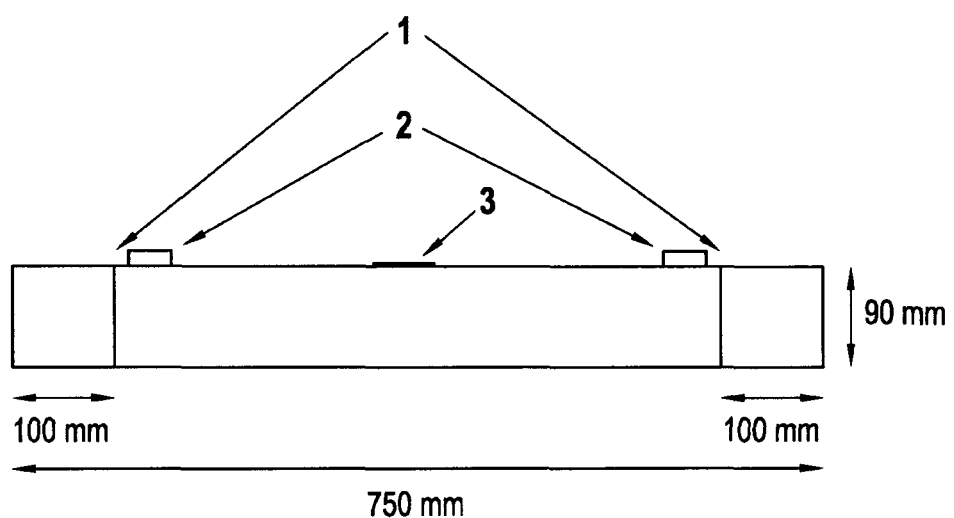

SYNERGISTIC FUNGICIDAL COMPOSITION AND METHODS OF USE

CROSS REFERENCE TO RELATED APPLICATIONS

This application claims priority to the following patent applications: (1) Patent Cooperation Treaty Application PCT/NZ2011/000119 filed Jun. 22, 2011; (2) New Zealand Application No. NZ586483 filed Jun. 29, 2010; and (3) New Zealand Application No. NZ593471 filed Jun. 15, 2011; each of the above cited applications is hereby incorporated by reference herein as if fully set forth in its entirety.

FIELD OF THE INVENTION

This invention relates to a synergistic fungicidal composition to its method of preparation, to its method of use and to products made therefrom. In particular, the invention relates to a wood preservative for glued wood products, and to its use in a method for the preservation of a glued wood product.

BACKGROUND OF THE INVENTION

Many plantation softwood species, generally members of the Pinaceae family, and certain hardwoods lack natural durability and are subject to rapid degradation by a host of insects and microorganisms that play a vital role in lignocellulosic mineralization and nutrient recycling processes in nature. Thus it is common practice to protect timber and other wood products using insecticides and fungicides.

The wood degrading microflora include bacteria and a large number of fungi of which the latter are the main cause of sapstain, mould and decay. Sapstain fungi and moulds produce unsightly superficial effects whereas decay fungi (also called rot fungi) severely weaken or completely break down wood.

White rot fungi are so called because they efficiently degrade all three principal wood cell wall biopolymers cellulose, hemicellulose and lignin, eventually producing a bleaching effect. Brown rot fungi are capable of utilising the cellulose and hemicellulose components, but only modifying the lignin component slightly, resulting in a darkening effect. Dry rot fungi are essentially brown rot fungi that can transport water into wood and decompose it slowly. A further category, the soft rot fungi, utilise cellulose and hemicellulose like brown rot fungi but their growth is restricted to inside the woody cell wall and the resulting damage becomes evident more slowly than with other decay fungi. Further information on wood decay fungi and their modes of action can be found in F. W. M. R. Schwarze "Wood decay under the microscope", 2007, Fungal Biology Reviews doi:10.1016/j.fbr.2007.09.001.

Traditional preservation systems include inorganic preservatives such as copper chrome arsenic, sodium octaborate and alkaline copper quaternary ("ACQ") that are introduced into timber in an aqueous medium, or carbon-based preservatives delivered in a non-aqueous medium termed a light organic solvent preservative ("LOSP"). These approaches achieve moderate levels of preservative penetration and result in generally effective protection but are expensive because they use vacuum and pressure to a greater or lesser extent, and must be performed in a separate step to other wood processing operations, thus incurring additional cost. Inorganic preservatives are loosing favour because of toxicity issues and the accompanying preservation methods require special care to avoid problems with dimensional stability. Persistent solvent residue problems characterise LOSP systems.

In recent years carbon-based preservatives and boron compounds have been incorporated into the glues and resins used to make engineered wood products, such as plywood and laminated veneer lumber, and reconstituted wood products such as particle board, oriented strand board and the like. While this system may be integrated easily into veneer and fibre lay up operations, it does require the preservative to be stable under extreme conditions such as heat (up to 250° C.), pressure and/or high pH (9-13) commonly encountered during layup and hot pressing of the wood product.

Glueline addition of biocides presents other challenges. The addition must not significantly change the working properties of the resin (viscosity, dynamic surface tension, etc) that affect pumping, curtain coating onto veneers or mixing with fibres, as well as other properties including wet bond strength (tack), curing rate and the like. Most importantly, the addition must not reduce the bond strength of the final product. It is therefore imperative to add the least possible amount of biocide to the adhesive that will prevent decay during the service life of the glued wood product.

Commercially significant decay fungi are dominated by the brown and white rots, some of which are susceptible to triazole fungicides such as tebuconazole and propiconazole. Tebuconazole and propiconazole are widely used in LOSP processes. However, unworkably high addition rates are required to achieve efficacy when tebuconazole and/or propiconazole are applied to the glues and resins used to make engineered and reconstituted wood products.

The effectiveness of a wood preservative in the field is limited by any point of weakness against individual fungal species. Accordingly, there is a need with respect to glueline application to increase triazole addition rates by some means, or in some other way overcome the weaknesses of triazole fungicides against certain fungi that can be problematic with glued wood containing products. It is also desirable to increase the efficacy against dry rots and soft rots. At the same time, health, safety and environment considerations are among factors driving a reduction in biocide concentrations in preservative-treated wood products.

The triazoles under consideration in this disclosure are summarised in Table 1. Triadimenol is the carbonyl reduced form of triadimefon. Triadimefon and triadimenol have similar physical properties apart from melting point and vapour pressure, and contain one and two chiral carbons, respectively. Cyproconazole has similar physical properties to tebuconazole and propiconazole in most respects but differs in the octanol-water partition coefficient ($K_{ow}$) and air-water distribution coefficient (Henry's law constant). These azoles contain two, one and two chiral carbons, respectively (Table 1). All of the listed triazoles are therefore present as various stereoisomeric mixtures.

The formulation types available for agricultural use (Pesticide Manual, 15th Edition, 2009) reflect in large part the ease of manufacture which is based on the different physical properties of the triazoles, their stability in different formulation types, and the crops and disease control profiles of these active ingredients. Accordingly triadimefon is formulated as powders, granule, paste or emulsifiable concentrate; triadimenol is formulated in a wide range including powders, granule, emulsions, suspensions, and concentrates. Cyproconazole is formulated as a concentrate, solution or granule; tebuconazole as a very wide range including powders, granule, emulsions, gel, suspensions, and concentrates.

Propiconazole, which as a technical is a liquid at ambient temperature, is formulated as an emulsion or gel.

are: triadimefon 77, triadimenol 113, cyproconazole 228, tebuconazole 10, propiconazole 55 (E. R. Trosken, M.

TABLE 1

Triazole structures and selected properties (The Pesticide Manual, 15th Edition, 2009).

| Compound | Triadimefon | Triadimenol | Cyproconazole |
|---|---|---|---|
| Structure | [structure] | [structure] | [structure] |
| Stereochemistry | Racemate | 70% A, 30% B | Racemate |
| Molecular weight | 293.8 | 295.8 | 291.8 |
| Form | Colourless crystals weak char. odour | Colourless odourless crystals | Colourless solid |
| Melting point | 82.3° C. | A 138.2° C., B 133.5° C. | 106.2-106.9° C. |
| Vapour pressure | 0.06 mPa | 0.0006 mPa | 0.026 mPa |
| $K_{ow}$ (log P) | 3.11 | A 3.08, B 3.28 | 3.1 |
| Henry (P m$^3$ mol$^{-1}$) | $9 \times 10^{-5}$ | A $3 \times 10^{-6}$, B $4 \times 10^{-6}$ | $2.6 \times 10^{-4}$ |
| Sol. Water | 64 mg/L (20° C.) | A 62 mg/L (20° C.) B 33 mg/L (20° C.) | 93 mg/L (22° C.) |
| Sol. DCM | >200 g/L (20° C.) | >250 g/L (20° C.) | 430 g/L (25° C.) |
| Sol. toluene | >200 g/L (20° C.) | 20-50 g/L (20° C.) | 100 g/L (25° C.) |
| Sol. hexane | 6.3 g/L (20° C.) | 0.1-1.0 g/L (20° C.) | 1.3 g/L (25° C.) |
| Stability | Stable to hydrolysis, $DT_{50} > 1$ y pH 4, 7, 9 | Stable to hydrolysis, $DT_{50} > 1$ y pH 4, 7, 9 | Stable in water 35 d at 50° C. pH 1-9 |

Triazole structures and selected properties (The Pesticide Manual, 15th Edition, 2009).

| Compound | Tebuconazole | Propiconazole |
|---|---|---|
| Structure | [structure] | [structure] |
| Stereochemistry | Racemate | 60% cis, 40% trans |
| Molecular weight | 307.8 | 342.2 |
| Form | Colourless crystals | Yellow odourless viscous liquid |
| Melting point | 105° C. | −23° C. (glas transition temp) |
| Vapour pressure | 0.0017 mPa | 0.027 mPa |
| $K_{ow}$ (log P) | 3.7 | 3.72 |
| Henry (P m$^3$ mol$^{-1}$) | $1 \times 10^{-5}$ | $9.2 \times 10^{-5}$ |
| Sol. Water | 36 mg/L (20° C.) | 100 mg/L (20° C.) |
| Sol. DCM | >200 g/L (20° C.) | Completely misc |
| Sol. toluene | 50-100 g/L (20° C.) | Completely misc |
| Sol. hexane | <0.1 g/L (20° C.) | 47 g/L (25° C.) |
| Stability | Stable to hydrolysis, $DT_{50} > 1$ y pH 4, 7, 9 | Stable to 320° C., no sign. hydrolysis |

The principal mode of action of triazole fungicides is inhibition of the biosynthesis of ergosterol, the major sterol found in fungal membranes. Binding of the triazole ring to cytochrome P450 sterol 14α-demethylase (CYP51) leads to an accumulation of 14α-methyl diols resulting in lethal disruption of fungal membrane integrity. Cytochrome P450 sterol 14α-demethylase is widely distributed among biological kingdoms and is responsible for 14α-demethylation of sterols in the biosynthesis of cholesterol in mammals, and in phytosterol and gibberellin biosynthesis in plants.

Selective inhibition of CYP51 is a key requirement for a triazole to be acceptable for timber preservation, agriculture and medicine. As an indication of relative selectivity of triazoles, the inhibitory potencies against human and yeast CYP51, expressed as a ratio of $IC_{50}$ values (human/yeast)

Adamska, M. Arand, J. A. Zarn, C. Patten, W. Volkel, and W. K Lutz "Comparison of lanosterol-14α-demethylase (CYP51) of human and *Candida albicans* for inhibition by different antifungal azoles", 2006, Toxicology 228, 24-32), i.e. triadimefon, triadimenol and propiconazole are moderately selective for the fungal enzyme, cyproconazole is highly selective, and tebuconazole very non-selective.

It is known that in many species of fungi, plants and mammals, and in soil, triadimefon is reduced to triadimenol in what is termed an "activation" process, i.e. for many fungal species triadimenol is the fungicidally active metabolite, and that the sensitivity of individual fungal species to triadimefon is related to the extent of activation. More particularly, the sensitivity of a fungal species to triadimefon (and triadimenol) is related to extent of conversion, the stereochemistry of the triadimefon reduction reaction, i.e. which enantiomers are formed and in what relative proportions, and the sensitivity of the fungal species in question to each of the individual triadimenol enantiomers formed (see for example, M. Gasztonyi "The diastereomeric ratio in the triadimenol produced by fungal metabolism of triadimefon, and its role in fungicidal selectivity", 1981, Pesticide Science 12, 433-438, and A. H. B. Deas, G. A. Carter, T. Clark, D. R. Clifford and C. S. James "The enantiomeric composition of triadimenol produced during metabolism of triadimefon by fungi: III. Relationship with sensitivity to triadimefon" 1986, Pesticide Biochemistry and Physiology 26, 10-21). It is well known that 1S,2R triadimenol is generally the most fungicidally active enantiomer.

Knowledge of the sensitivity of individual fungal species to triadimefon (and triadimenol) was most comprehensively disclosed by Deas et al. (cited above) who analysed the stereospecific metabolism of triadimefon and the sensitivity to each of the four triadimenol metabolites of fifteen fungal species, predominantly plant pathogens (i.e. cellulolytic) and also including two white rot decay organisms (*Coriolus versicolor*, now commonly known as *Trametes versicolor*, and *Chondrostereum purpureum*), and a highly cellulolytic mould active on wood (*Trichoderma viride*). The fungi were divided broadly into three categories to explain the sensitivity of different fungal species to triadimefon. In one category, which included *Coriolus versicolor* and *Chondrostereum purpureum*, fungi were sensitive to both triadimefon and triadimenol, and the triadimefon sensitivity appeared to be based on a high rate of triadimefon conversion and the 1S,2R enantiomer being the major contributor to the fungicidal activity among the triadimenol metabolites produced. In a further category, which included *Trichoderma viride*, fungi were insensitive to triadimefon and triadimenol, and converted triadimefon to forms of triadimenol dominated by enantiomers that the fungi were not sensitive to. In a still further category fungi were comparatively insensitive to triadimefon but partially sensitive to triadimenol. The latter fungi displayed either a high extent of triadimefon conversion but low sensitivity to the particular triadimenol enantiomers produced, or a low extent of conversion even though very sensitive to the enantiomers produced, both scenarios combining to produce the net effect of comparative insensitivity to triadimefon. Deas et al. also found no evidence of antagonism or synergy among the various triadimenol enantiomers.

The Pesticide Manual discloses that technical grade triadimenol comprises 70% A and 30% B. Deas et al (cited above) disclose a different enantiomeric composition (1R, 2S:1S,2R:1R,2R:1S2S=21:21:29:29. Notwithstanding this difference, and considering the foregoing discussion, it should be noted that technical grade triadimenol comprises about 21-35% of the generally highly potent 1S,2R enantiomer.

In accordance with the foregoing discussion it has been found that triadimenol controls a much broader spectrum of agricultural fungal pathogens and consequently is more widely used than triadimefon. Triadimenol also controls a number of wood degrading fungi at significantly lower concentrations than triadimefon. However, the inhibitory concentration of either active ingredient acting alone varies up to 50-fold or more when tested against a range of organisms (see, for example, EP 0254857). The minimum concentrations of active ingredients required for effective timber preservation are determined by the organisms that are least sensitive to the preservative. Thus the minimum effective dose for preservation in service is dictated by those species most resistant to a particular active ingredient.

As noted above any single active ingredient will have less effectiveness against certain fungal species. This is counteracted by combining two (or more) active ingredients to provide more effective control of fungal growth at cost effective doses against a broad spectrum of different fungal organisms.

All references, including any patents or patent applications cited in this specification are hereby incorporated by reference. The applicant makes no admission that any reference constitutes prior art—they are merely assertions by their authors and the applicant reserves the right to contest the accuracy, pertinence and domain of the cited documents. None of the documents or references constitutes an admission that they form part of the common general knowledge in NZ or in any other country.

Applicants disclose that, surprisingly, triadimenol displays an antagonistic interaction with cyproconazole with respect to fungicidal activity, whereas triadimefon displays a synergistic interaction with cyproconazole. This is entirely unexpected and surprising when it is considered that in most if not all cases where triadimefon is fungicidal against a particular fungal species, it is actually triadimenol, the metabolite of triadimefon, that is recognised as being the fungicidally active factor, not triadimefon itself. The fact that triadimenol is the active factor is recognised in the art. It is therefore totally unanticipated that triadimefon will have a synergistic interaction with cyproconazole when triadimenol, the active metabolite of triadimefon, itself displays an antagonistic interaction with cyproconazole.

The synergy observed with triadimefon and cyproconazole is all the more surprising when it is seen that triadimefon acting alone is less efficacious than triadimenol acting alone.

The net effect of this research is the enablement of improved protection of wood and glued wood products against a broad range of decay fungi and a lowering of rates of fungicidal addition to achieve such control.

OBJECT OF THE INVENTION

It is an object of the invention to provide an improved composition and/or preparative method thereof and/or use thereof which will obviate or minimize one or more of the previously mentioned disadvantages, or provide one or more of the previously mentioned desirable features, or which will at least provide the public with a useful choice.

SUMMARY OF THE INVENTION

In a broad aspect the invention is directed to a broad spectrum, synergistic fungicidal composition characterised in that the composition comprises a synergistically effective amount of the active ingredients (A) triadimefon and (B) cyproconazole.

Preferably, the broad spectrum, synergistic fungicidal composition is used as a glueline preservative for glued wood products characterised in that the composition comprises a synergistically effective amount of the active ingredients (A) triadimefon and (B) cyproconazole In one aspect the fungicidal composition comprises (A) triadimefon and (B) cyproconazole as active ingredients, in triadimefon:cyproconazole weight ratios from about 20:1 to about 1:1, sufficient to provide a synergistic fungicidal activity when used against wood degrading fungi.

The broad spectrum, synergistic fungicidal composition is particularly efficacious when used as a glueline preservative. The synergy observed between triadimefon and cyproconazole is even more unexpected in this application because other triazoles are recognised as being ineffective in a glueline environment unless they are delivered at unworkable and uneconomically high levels or at levels that detrimentally compromise the integrity of the glue.

The surprising synergy between the active ingredients (A) triadimefon and (B) cyproconazole allows the effective rates of fungicide required to be lowered producing a number of improved benefits. The synergistic composition applied to the glueline of engineered wood products, for example, is surprisingly much more effective than commercially acceptable LOSP treatments. Furthermore the synergistic composition produces effective control of a broader range of fungal species at reduced cost than existing preservative treatments. A reduction in application rates minimises perturbation of glue working properties and bond strength and lowers environmental and occupational health and safety concerns associated with treatment.

In one broad aspect this invention provides synergistic fungicidal compositions suitable for use as a glueline preservative comprising (A) triadimefon and (B) cyproconazole as active ingredients.

In a further broad aspect this invention provides methods of formulating synergistic fungicidal compositions for use in a glueline environment.

In a further broad aspect this invention provides a method for the preservation of glued wood products, which comprises applying fungicidally effective amounts of the broad spectrum, synergistic fungicidal composition to the glue component of glued wood products.

In a yet further broad aspect the broad spectrum, synergistic fungicidal composition may be applied as an optional additional surface treatment for a glued wood product either simultaneously or sequentially.

BRIEF DESCRIPTION OF THE DRAWING

FIG. 1 is a side view of wood specimens for testing the preservative compositions of the present invention.

DETAILED DESCRIPTION

This invention relates generally to combinations of fungicidal active ingredients and more particularly to broad spectrum, synergistic compositions of fungicidal active ingredients intended to provide more effective and broader control of decay microorganisms in wood products, and in particular, in glued wood products.

Unless defined otherwise, all technical and scientific terms used herein have the same meaning as commonly understood by one of ordinary skill in the art to which this invention belongs.

The term "fungicidal" encompasses all effects on fungi including but not limited to the destruction or killing of fungi, a defined logarithmic reduction, a partial or complete suppression or inhibition of growth, inhibition of germination, and the like. The term "fungicidally effective amount" indicates the quantity or application rate of a fungicidal composition or of a fungicidal active ingredient which is capable of producing any one or more such effects.

The term "glue" is used as a general term for any product used in the manufacture of wood products resulting in permanent or semi-permanent adhesion, bonding, chemical bonding, linkage, attachment, etc, of wood or wood derived components such as sawn timber, veneers, flakes, fibres, and the like. "Glue" includes terms such as adhesive, resin, tackifier, glue mix, glue mixture, glue component, and the like, and these terms may be used interchangeably in this disclosure. The introduction of a wood preservative to the glue component of a glued wood product is commonly referred to as a "glueline" treatment, and this term may be used whether the glue is present in a defined zone such as a veneer interface, or the glue is more widely distributed throughout the product as it is in a reconstituted wood product such as oriented strand board. Furthermore, a glueline preservative may also be introduced into the glueline by spraying or misting the preservative directly on to veneers, chips, flakes, etc prior to or during the layup operation. The preservative remains subject to potential chemical and/or thermal decomposition effects in the presence of the glue component during subsequent manufacturing processes.

The term "synergistic" refers to a particular phenomenon that occurs when the observed fungicidal effect of a mixture of active ingredients is unexpectedly greater than might be expected from the sum of the observed fungicidal effects of the active ingredients administered separately. Synergy may be calculated in various ways, generally based on fungicide concentrations that produce a defined end point in measured fungal growth, or in measured or otherwise evaluated effects resulting from the fungal growth. Examples of such measurements or evaluated effects include colony diameter, percentage germination, weight loss of a piece of infected wood, softening or weakening of a piece of infected wood, and estimations of fungal infection based on coverage and density of fungal growth. Any of these and other parameters can be enumerated using an instrument and/or evaluated manually or visually and assigned to linear or non-linear rating scales.

Methods that may be used to calculate synergy include those described by Y. Levy, M. Benderly, Y. Cohen, U. Gisi, and D. Bassand ("The Joint Action of Fungicides in Mixtures: Comparison of Two Methods for Synergy Calculation", 1986, Bulletin OEPP, 16, 651-657), by F. C. Kull, P. C. Eisman, H. D. Sylwestrowicz, and R. L. Mayer ("Mixtures of Quaternary Ammonium Compounds and Long-chain Fatty Acids as Antifungal Agents", 1961, Applied Microbiology, 9, 538-541), and by R. S. Colby ("Calculating Synergistic and Antagonistic Responses of Herbicide Combinations", 1967, Weeds 15, 20-22).

In contrast an "antagonistic" effect refers to the situation whereby two or more components produce a combined effect which is less than the sum of their individual parts.

Surprisingly, we have found that a fungicidal composition comprising as active ingredients triadimefon and cyproconazole in weight ratios from about 20:1 to about 1:1, and more preferably, from about 20:1 to about 6:1, yields synergistic fungicidal activity against wood degrading fungi, i.e. the fungicidal effects and/or the resulting effects on glued wood products by the combinations of active ingredients are unexpectedly greater than the expected effects based on the effects of the individual active ingredients administered separately. The effective application rates required can be lowered as a result of the synergy making the resulting products and protection systems for timber and wood products more economical, and minimising or eliminating one or more of the previously mentioned problems.

If the active ingredients in the synergistic composition according to the invention are present in certain weight ratios, the synergistic effect is particularly pronounced. However, the weight ratios of the active ingredients in the synergistic composition can be varied within a relatively wide range. The ratios of triadimefon to cyproconazole indicated in this disclosure do not in any way limit the scope of this invention, but rather are mentioned as a guide, a person of ordinary skill in the art being capable of carrying out complementary experiments in order to find other values of the ratios of active ingredients which produce a synergistic effect.

The synergistic fungicidal composition comprising triadimefon and cyproconazole may be used to control a broad range of decay organisms including those causing white rot, brown rot, dry rot and soft rot, as well as provide beneficial antifungal activity against sapstain organisms and moulds.

Examples of fungi active on wood include but are not limited to ascomycetes, basidiomycetes and deuteromycetes. The brown rots include *Antrodia xantha, Antrodia vaillantii, Coniophora olivacea, Coniophora puteana, Fomitopsis lilacino-gilva, Gloeophyllum abietinum, Gloeophyllum odoratum, Gloeophyllum sepiarium, Gloeophyllum trabeum, Lentinus lepideus, Neolentinus lepideus, Paxillus panuoides, Polyporus verecundus, Poria monticola, Poria placenta, Poria vaillantii, Poria vaporaria, Postia placenta*, and *Tyromyces palustris*. The white rots include *Ceriporiopsis subvermispora, Coriolus versicolor, Donkioporia expansa, Irpex lacteus, Lentinus edodes, Lopharia crassa, Phanerochaete chrysosporium, Pleurotus ostreatus, Perenniporia tephropora, Pycnoporus coccineus, Stereum hirsutum*, and *Trametes versicolor*. The dry rot fungi include *Serpula himantioides, Serpula lacrymans, Cephalosporium* sp. and *Meruliporia incrassate*. The fungi that cause soft rots include *Acremonium* sp., *Alternaria* sp., *Chaetomium albaarenulum, Chaetomium globosum, Glenospora graphii, Humicola grisea, Petriella setifera* and *Trichurus spiralis*.

According to the invention, synergistic combinations of triadimefon and cyproconazole may be found when the relative amounts of triadimefon and cyproconazole expressed as a ratio triadimefon:cyproconazole are present within the range from about 20:1 to about 1:1 parts by weight. Preferably triadimefon and cyproconazole are present in a ratio from about 20:1 to about 2.5:1 parts by weight. More preferably triadimefon and cyproconazole are present in a ratio from about 20:1 to about 5:1 parts by weight. More preferably triadimefon and cyproconazole are present in a ratio from about 15:1 to about 5:1 parts by weight. Still more suitably triadimefon and cyproconazole are present in a ratio from about 15:1 to about 6:1 parts by weight.

The composition may comprise 0.1% to 60% triadimefon and 0.1% to 60% cyproconazole on a weight/weight basis or a weight/volume basis. The percentages of active ingredients in the composition will depend mainly on the formulation type, the nature and quantities of the glue system relative to the wood component, veneer thicknesses, wood strand dimensions, etc, blending or mixing equipment and processes, as well as the identity and quantities of other glueline additives such as waxes etc, that may be used for the particular glued wood products to which the composition is to be applied. An important consideration is the ease with which the composition can be dispensed accurately into the glue mixture.

This invention provides methods of formulating synergistic fungicidal compositions adapted specifically for use in a glueline environment.

The fungicidal composition is characterised in being readily dispersed into the glue component or the glueline environment during manufacture of glued wood products, or dispersed within the flakes, strands, fibres, etc, of reconstituted wood products. The dispersibility of the composition is in turn determined by the formulation type and the nature of the solvent base for the composition, as well as the presence of surfactants and other dispersal aids, as is known in the art.

Formulation types and methods of manufacture developed for crop protection purposes are generally used for preservatives for timber, wood and other biodegradable products. These are described, for example, in "Chemistry and Technology of Agrochemical Formulations", 1998, D. A. Knowles (editor), Kluwer Academic Publishers, "Pesticide Formulation and Adjuvant Technology", 1966, C. L. Foy (editor), CRC Press, and "Formulation Technology: Emulsions, Suspensions, Solid Forms", 2001, H. Mollet and A. Grubenmann, Wiley-VCH.

Advantageously, the formulation is a liquid thus minimising exposure of users to the hazards of powders and dusts. When needed for use with dry glue components, the formulation is a dry mixture, preferably a dust free formulation. Suitable formulation types for the fungicidal composition include, but are not limited to, a powder, a granule, a concentrate, a gel, a solution, an emulsion, a dispersion, a suspension, or a controlled release form including a microcapsule. Preferred formulation types are a suspension concentrate, an emulsion, a granule and a powder.

In addition to triadimefon and cyproconazole, the fungicidal composition may contain 0.1% to 99% of customary formulation additives. Customary formulation additives and their functions are described in the previously mentioned publications. Such additives may include water, suitable surfactants, dispersants, emulsifiers, penetrants, spreaders, wetting agents, soaps, carriers, oils, solvents, diluents, inert components, conditioning agents, colloids, suspending agents, thickeners, thixotropic agents, polymers, emollients, acids, bases, salts, organic and inorganic solid matrices of various kinds, preservatives, anti-foam agents, anti-freeze agents, anti-caking agents, lubricants, stickers, binders, complexing agents, chelating agents, crystallization inhibitors, dyes, activators, and the like.

Certain additives are known to increase the efficacy of fungicidal active ingredients for wood preservation, for example compounds that assist in the movement of active ingredients into the wood component at any stage during and after the manufacturing process. Such compounds include but are not limited to surfactants, chelating agents and various solvent modifiers including aprotic solvents. Suitable aprotic solvents comprise cyclic ethers including 1,4-dioxane, tetrahydropyran, tetrahydropyran and the like, short chain aliphatic ethers, unsaturated ethers such as mesityl oxide, alkyl aryl ethers such as acetophenone, diaryl ethers, glycol ethers, and alkylene glycol ethers, ketones such as methylethyl ketone, methylpropyl ketone, cyclopentanone, cyclohexanone and the like, lactones such as propiolactone, butyrolactone, valerolactone and the like, dialkyl carbonates, amides such as dimethylformamide, diethylformamide, dimethylacetamide, dimethylbutyramide and the like, lactams and derivates thereof including 1-methyl-2-pyrrolidone, 1-ethyl-2-pyrrolidone and the like, short chain trialkylamines, quinoline, pyrimidine, N-methylpiperidine, and the like. Also suitable as penetration aids are alcohols and glycols, alkanolamines, quaternary ammonium compounds, imines and amine oxides.

Further biocidal active ingredients may be combined with the fungicidal active ingredients of the composition including other fungicides, mouldicides, anti-sapstain compounds, insecticides, bactericides, algaecides, and the like. Preferably the additional biocidal ingredient is one or more insecticides.

Compositions are formulated using known methods by dissolving, dispersing, finely dividing, slurrying, blending, emulsifying, homogenizing, stirring, high-shear mixing, comminuting, milling, stabilising, etc, the active ingredients, and by admixing with appropriate quantities of the one or more previously mentioned customary formulation additives to form the composition of the invention. In addition triadimefon and/or cyproconazole may be microencapsulated prior to mixing with other formulation additives. Further details of suitable methods of manufacture of the composition are provided in the examples.

Where applicable to the compositions formulated using the known methods referred to above and as provided in methods of the examples, the mean particle size as determined for example using a laser diffraction particle size analyser after dilution into water, is from about 0.1 microns to about 50 microns. Preferably the mean particle size is from about 0.1 microns to about 20 microns. Still more preferably the mean particle size is from about 0.2 microns to about 5 microns.

The invention provides a method of preservation of glued wood products, which comprises applying to the glue component of such products, fungicidally effective amounts of a synergistic fungicidal composition comprising triadimefon and cyproconazole as active ingredients.

Advantageously the composition of the invention is incorporated into the glues and resins used to make glued wood products including various engineered wood products, reconstituted wood products and combinations thereof. The starting materials for such products encompass solid wood, timber or lumber, veneers of various thicknesses, wood flakes, chips, strands, particles, fibres, flour, dusts or nanofibrils, including chemically and/or thermally modified derivatives thereof. Engineered wood products comprise glued solid timber or glued wood veneers and include products such as glued laminated timber (for example, Glulam and Mabashira), laminated veneer lumber (LVL) and plywood. Reconstituted wood products comprise glued wood flakes, chips, strands, particles, fibres, flour, dusts or nanofibrils, and include products such as strand board, oriented strand board, parallel strand lumber, flake board, particle board, medium density fibreboard (MDF), high density fibreboard, hardboard, combination products such as Triboard which comprises a strand board core with surface MDF layers, and wood plastic composites. Included in the scope of the invention are further combination products such as plywood in which one or both surface layers comprise a layer of MDF, another reconstituted wood product, a decorative veneer or a piece of solid wood. These surface layers may be introduced during normal lay up operations prior to hot pressing or may be added in gluing operations subsequent to manufacture of the base product. Also encompassed within the invention are other glued lignocellulosic products including glued products based on bamboo, rattan, bagasse, straw, hemp, jute sticks, flax shives and the like.

Glue types suitable for the invention consist of various organic polymers including amino resins, phenolic resins, isocyanate resins, epoxy resins, PVA adhesives, polyurethane glues, protein and protein-derived adhesives, starches, lignocellulosic extractives and other thermosetting biomaterials of renewable origin. The glue mixtures may be used in a liquid or non-liquid (dry) state. Excluded from the invention are adhesives when used to adhere wood products to other materials such as metal, plastics, etc.

Useful amino resins include urea and/or melamine derivatives including hydroxymethyl or alkoxymethyl derivatives of urea, melamine, benzoguanamine, and glycoluril, chiefly urea-formaldehyde (UF) resins, melamine-formaldehyde (MF) resins, melamine-urea formaldehyde (MUF) resins. These are produced by reaction of widely varying ratios of amine (urea, melamine, benzoguanamine, glycoluril), formaldehyde and alcohol under differing reaction conditions to produce a very broad range of resins suitable for gluing wood products. Useful phenolic resins comprise novolac-type and resole-type phenol-formaldehyde resins, resorcinol-formaldehyde resins and phenol-resorcinol-formaldehyde resins. Suitable isocyanate resins are based on (partially) polymerised diisocyanates, mainly polymeric diphenylmethane diisocyanate (pMDI). PVA adhesives contain polyvinyl acetate and polyvinyl alcohol in various mixtures, and other cross-linkable copolymers thereof. Polyurethane adhesives, both one part and two part, may be used alone or in combination with coupling agents. Protein based adhesives, including a wide range of adhesives manufactured from modified proteins and crosslinked proteins, including modified and/or crosslinked soy proteins, are particularly suitable for use with the invention. These products are gaining acceptance as formaldehyde-free adhesives suitable for glued wood products. Also included are mixed adhesives such as soy protein-modified amino and phenolic resins.

The glue mixture to which the composition of the invention is applied may also contain catalysts, plasticizers, wetting agents, inorganic and organic fillers and extenders (generally lignocellulosic residues), as well as other additives with various functions.

Most often the abovementioned glue types are hot-cured but some, e.g. PVA adhesives, polyurethanes and epoxy resins, cure at ambient temperatures. Pressure is usually combined with hot cure and cold cure processes.

With some exceptions, notably isocyanate resins and epoxy resins, water is the solvent acting as carrier for the adhesive and the fungicidal active ingredients of the composition. Non-aqueous adhesive solvents that are compatible with the glue system may also be used with the composition, including certain alcohols, ketones and glycol ethers, as long as the amounts used do not adversely affect working and curing properties of the glue.

Advantageously the fungicidal composition may be incorporated directly into the glue mixture prior to "lay up", the process whereby wood raw materials are arranged and combined with the glue mixture prior to the curing process. In this case the glue mixture containing the composition may be applied by pumping, blending, extruding, soaking, dipping, spinning, atomising, spraying, pouring, rolling, foaming, or curtain coating.

The fungicidal composition may be sprayed, misted or otherwise coated directly on to veneers, flakes, fibres, pieces of sawn timber and the like at any stage prior to the additional of the glue component. The essential requirement of the method is that the composition is delivered into the same final zone as the glue component.

In some situations, particularly with reconstituted wood products, the fungicidal composition may be applied directly to the wood raw material, sometimes termed the "furnish", by injection into a refiner, blow line, strand or chip tumbler, often in mixture with waxes and other agents, prior to, at the same time or after introduction of the glue mixture. This approach may be used for example with reconstituted wood products containing pMDI in order to minimise the water contact time for the pMDI component. In this case the composition is mixed rapidly into the glue component of the glued wood product by intimate mixing within the refiner or blow line prior to the curing reaction and, as such, is a glueline fungicide treatment.

The active ingredients of the composition together with other additives are preferably pre-formulated as a single composition. However, it should be emphasised that active ingredients of the composition may also be formulated separately and incorporated into the glue prior to application, or may be applied sequentially to the wood components prior to the addition of glue components, and that these scenarios falls within the scope of the invention.

The fungicidal composition is administered to the glue mixture, or furnish, in sufficient amounts to achieve desired concentrations or loadings of active ingredients in the finished product taking into account the relative amounts of glue and wood component. The calculated active ingredient loading, as well as the concentration of active ingredient recovered from the finished product and measured by an analytical procedure (termed the active ingredient "retention"), may be expressed as grams of active ingredient per cubic meter of dried wood product (gai/m$^3$) or mass of active ingredient/mass of dried wood product (% m/m). A minimum retention of an active ingredient may be specified with reference to a particular "hazard class" for the finished product, i.e. a category relating to the durability of the product in a defined geographical area, the location of the product in a building or structure, its exposure to moisture, proximity to the ground, etc. The minimum retention and other defined parameters are determined based on results of standard durability test methods set by organisations such as Australasian Wood Preservation Committee (AWPC), American Wood Preservers Association, Japanese Industrial Standards, EN Standards etc.

Use rates for the composition of the invention vary within the range from about 5 gai/m$^3$ to about 5,000 gai/m$^3$ for triadimefon and within the range from about 5 gai/m$^3$ to 5,000 gai/m$^3$ for cyproconazole, depending on the nature of the glued wood product, and the hazard class for the product. Preferably the use rates vary within the range from about 50 gai/m$^3$ to about 5,000 gai/m$^3$ for triadimefon and within the range from about 5 gai/m$^3$ to about 1,000 gai/m$^3$ for cyproconazole. Still more preferably the use rates for triadimefon vary within the range from about 100 gai/m$^3$ to about 5,000 gai/m$^3$ and the use rates for cyproconazole within the range from about 10 gai/m$^3$ to about 1,000 gai/m$^3$, depending on the nature of the glued wood product, and the hazard class for the product.

Optionally the composition may be used as a surface treatment in addition to a glueline treatment for glued wood products in order to provide an extra line of defence against fungal attack. In this instance the composition may be applied to the surface by spraying, dipping, painting, pouring, rolling, and the like.

EXAMPLES

It will be appreciated that the compositions are provided as non-limiting examples only and that other synergistic fungicidal compositions comprising triadimefon and cyproconazole as active ingredients will also fall within the ambit of the instant invention.

Example 1

Slowly blend 210.5 grams of triadimefon (95% tech) and 21.3 grams of cyproconazole (94% tech) into 100 mL water containing 40 grams of commercially available rheology modifiers and dispersants. Add more water until a smooth slurry is formed then mill the mixture to achieve an average particle size less than 5 microns. Add 1.5 grams of a commercially available thickening agent. Stir until full viscosity is reached, add 2 grams of isothiazolinone biocide then make up to 1,000 mL with water. The resulting suspension concentrate containing 200 grams/liter triadimefon and 20 grams/liter cyproconazole can be diluted with water or added directly to glue mixtures for use in glued wood products.

Example 2

Hammer mill 421 grams of triadimefon (95% tech) and 42.6 grams of cyproconazole (94% tech), then mix in a ribbon blender with 30 grams commercially available anionic dispersants and 506.4 grams of powdered silica until homogeneous. The resulting dispersible powder containing 40.0% (w/w) triadimefon and 4.0% (w/w) cyproconazole can be blended into powdered resins or dispersed into liquid glue mixtures for use in glued wood products.

Example 3

Hammer mill 421 grams of triadimefon (95% tech) and 42.6 grams of cyproconazole (94% tech), then mix in a ribbon blender with 100 grams commercially available anionic dispersants and 420.0 grams of China clay until homogeneous. Add 10% to 15% water and knead in a Z mixer until a moist powder is formed that just holds together. Extrude through a cone extruder and dry in a fluid bed drier to about 1 to 2% moisture content. The resulting dispersible extruded granule containing 40.0% (w/w) triadimefon and 4.0% (w/w) cyproconazole can be dispersed into liquid glue mixtures for use in glued wood products.

In the following examples, the synergistic fungicidal effects of compositions comprising triadimefon and cyproconazole as active ingredients are demonstrated in various biological assays. Synergy was determined by the "Wadley method" for similar joint action as disclosed by Y. Levy, M. Benderly, Y. Cohen, U. Gisi, and D. Bassand ("The joint action of fungicides in mixtures: comparison of two methods for synergy calculation", 1986, Bulletin OEPP 16, 651-657), according to the formulae:

$$ED(\exp) = (a+b)/(a/ED_A + b/ED_B), \qquad 1.$$

in which,
$ED_A$ is the concentration in ppm of (A), acting alone, which produced an end point,
$ED_B$ is the concentration in ppm of (5), acting alone, which produced an end point,
a and b are the proportions of (A) and (B) in the mixture, and
ED(exp) is the expected equally effective concentration in ppm of (A) and (B), acting together, in the proportions a and b, and $$SF = ED(\exp)/ED(\text{obs}), \qquad 2.$$

in which,
SF is the synergy factor, and
ED(obs) is the observed equally effective concentration in ppm of (A) and (B), acting together, in the proportions a and b.

If SF>1, there is synergistic interaction between the fungicides,
if SF<1, there is antagonistic interaction, and
if SF=1, there is additive action (i.e. similar joint action).
The end points used were $EC_{90}$ or $EC_{50}$, the concentration producing 90% or 50% inhibition of growth or weight loss resulting from fungal growth. EC values were calculated by regression analysis of dose response data using the GraphPad Prism software package (GraphPad Software, Inc., 5755 Oberlin Drive #110, San Diego, Calif. 92121, USA). $EC_{90}$ values are expressed in ppm and $EC_{50}$ values are expressed in gai/m$^3$.

Example 4

Decay fungi were grown on malt extract agar plates for 5 days at 25° C. in the presence of triadimefon alone or triadimenol alone (A), cyproconazole alone (B), and the pairs of mixtures shown in Table 2.

TABLE 2

Combined action of triadimefon/cyproconazole or triadimenol/cyproconazole on decay fungi.

| Fungicide | $EC_{90}$ (obs) | $EC_{90}$ (exp) | SF | Fungicide | $EC_{90}$ (obs) | $EC_{90}$ (exp) | SF |
|---|---|---|---|---|---|---|---|
| *Antrodia xantha* (Brown rot) | | | | | | | |
| Triadimefon | 2.56 | | | Triadimenol | 1.12 | | |
| 20:1 | 0.34 | 1.60 | 4.73 | 20:1 | 1.24 | 0.91 | 0.73 |
| 10:1 | 0.52 | 1.19 | 2.29 | 10:1 | 1.14 | 0.77 | 0.68 |
| 5:1 | 0.63 | 0.82 | 1.31 | 5:1 | 1.15 | 0.61 | 0.53 |
| Cyproconazole | 0.19 | | | Cyproconazole | 0.19 | | |
| *Fomitopsis lilacino-gilva* (Brown rot) | | | | | | | |
| Triadimefon | 1.48 | | | Triadimenol | 0.37 | | |
| 20:1 | 0.38 | 0.97 | 2.57 | 20:1 | 0.43 | 0.34 | 0.79 |
| 5:1 | 0.46 | 0.52 | 1.12 | 5:1 | 0.38 | 0.28 | 0.72 |
| Cyproconazole | 0.12 | | | Cyproconazole | 0.12 | | |
| *Trametes versicolor* (White rot) | | | | | | | |
| Triadimefon | 1.52 | | | Triadimenol | 0.15 | | |
| 20:1 | 0.21 | 1.27 | 6.17 | 20:1 | 0.16 | 0.15 | 0.95 |
| 10:1 | 0.57 | 1.11 | 1.96 | 10:1 | 0.16 | 0.15 | 0.93 |
| 5:1 | 0.49 | 0.90 | 1.84 | 5:1 | 0.18 | 0.15 | 0.88 |
| Cyproconazole | 0.30 | | | Cyproconazole | 0.19 | | |

Triadimenol acting alone was two to ten times more efficacious than triadimefon acting alone, consistent with existing prior knowledge that triadimenol is the active metabolite of triadimefon. Mixtures of triadimefon and cyproconazole in ratios ranging from 20:1 to 5:1 were synergistic whereas mixtures containing triadimenol and cyproconazole were antagonistic. This is very surprising given that the prior knowledge that triadimenol is the active metabolite of triadimefon, and even more surprising given the demonstration that triadimefon alone is less efficacious than triadimenol alone. As a result of the unexpected synergy, the largest $EC_{90}$ value (the weakest point) among the triadimefon-cyproconazole mixtures was 0.63 ppm (*Trametes versicolor*). This was less than half of the $EC_{90}$ values for all of the triadimenol-cyproconazole mixtures for *Antrodia*. It must be noted that even though cyproconazole alone was more effective than the other treatments, timber preservation with a single active ingredient is always vulnerable to attack by certain fungal species less susceptible to the single active ingredient, and does not provide for the desired broad spectrum efficacy.

Example 5

Further $EC_{90}$ values were determined as in Example 4. Triadimenol acting alone was more potent than triadimefon acting against three of the four fungi, the exception being the dry rot organism *Serpula lacrymans* (Table 3). The triadimefon cyproconazole mixture was synergistic for all fungi, and the triadimenol cyproconazole mixture was antagonistic for all apart from *Gloeophyllum abietinum*, where it was approximately additive. As a result of the synergy the largest $EC_{90}$ value (the weakest point) for the triadimefon cyproconazole mixture was 8.3 ppm (*Serpula lacrymans*), much lower than the corresponding value for triadimenol cyproconazole, and illustrates conclusively that triadimefon cyproconazole is the better broad spectrum fungicide.

TABLE 3

Combined action of triadimefon/cyproconazole or triadimenol/cyproconazole on decay fungi.

| Fungicide | $EC_{90}$(obs) | $EC_{90}$(exp) | SF | Fungicide | $EC_{90}$(obs) | $EC_{90}$(exp) | SF |
|---|---|---|---|---|---|---|---|
| *Pycnoporus coccineus* (White rot), 4 days growth | | | | | | | |
| Triadimefon | 0.34 | | | Triadimenol | 0.10 | | |
| 20:1 | 0.25 | 0.33 | 1.32 | 20:1 | 0.48 | 0.10 | 0.21 |
| Cyproconazole | 0.17 | | | Cyproconazole | 0.17 | | |
| *Tyromyces palustris* (Brown rot), 4 days growth | | | | | | | |
| Triadimefon | 4.48 | | | Triadimenol | 1.26 | | |
| 20:1 | 2.75 | 3.54 | 1.29 | 20:1 | 2.90 | 1.21 | 0.42 |
| Cyproconazole | 0.68 | | | Cyproconazole | 0.68 | | |
| *Poria placenta* (Brown rot), 5 days growth | | | | | | | |
| Triadimefon | 0.82 | | | Triadimenol | 0.84 | | |
| 20:1 | 0.69 | 0.83 | 1.20 | 20:1 | 1.83 | 0.85 | 0.46 |
| Cyproconazole | 0.92 | | | Cyproconazole | 0.92 | | |
| *Gloeophyllum abietinum* (Brown rot), 7 days growth | | | | | | | |
| Triadimefon | 17.2 | | | Triadimenol | 1.80 | | |
| 20:1 | 0.61 | 4.12 | 6.77 | 20:1 | 1.36 | 1.40 | 1.02 |
| Cyproconazole | 0.25 | | | Cyproconazole | 0.25 | | |
| *Serpula lacrymans* (Dry rot), 5 days growth | | | | | | | |
| Triadimefon | 26.4 | | | Triadimenol | 42.8 | | |
| 20:1 | 8.32 | 15.2 | 1.83 | 20:1 | 102 | 19.20 | 0.19 |
| Cyproconazole | 1.60 | | | Cyproconazole | 1.60 | | |

Example 6

$EC_{90}$ values for triadimefon and cyproconazole acting alone and together in a 1:1 mixture, determined as in Examples 4 and 5, further demonstrate the range of the synergistic interaction between these two fungicides (Table 4).

TABLE 4

Combined action of triadimefon and cyproconazole on decay fungi.

| Fungicide | $EC_{90}$ (obs) | $EC_{90}$ (exp) | SF |
|---|---|---|---|
| Pycnoporus coccineus (White rot), 6 days growth | | | |
| Triadimefon | 0.70 | | |
| 1:1 | 0.20 | 0.23 | 1.15 |
| Cyproconazole | 0.14 | | |
| Poria placenta (Brown rot), 6 days growth | | | |
| Triadimefon | 1.08 | | |
| 1:1 | 0.43 | 0.54 | 1.26 |
| Cyproconazole | 0.36 | | |
| Antrodia xantha (Brown rot), 8 days growth | | | |
| Triadimefon | 2.52 | | |
| 1:1 | 0.67 | 0.78 | 1.16 |
| Cyproconazole | 0.46 | | |
| Coniophora puteana (Brown rot), 8 days growth | | | |
| Triadimefon | 27.4 | | |
| 1:1 | 2.45 | 3.61 | 1.47 |
| Cyproconazole | 1.93 | | |
| Serpula lacrymans (Dry rot), 8 days growth | | | |
| Triadimefon | 26.3 | | |
| 1:1 | 2.04 | 2.52 | 1.23 |
| Cyproconazole | 1.32 | | |

Example 7

Efficacy as a glueline fungicide was tested in plywood manufactured with phenol formaldehyde (PF), a typical resin used in engineered wood products. The wood type was *Pinus radiata* sapwood, which, like many softwoods, is rapidly degraded by decay organisms, if not protected. Five 3.2 mm rotary-peeled veneers were laid up with fungicide-containing PF resin at a typical commercial glue spread rate (250 g/m$^2$), cold pressed for 10 minutes then hot pressed for 12 minutes at 135° C. and 50 MPa. Test specimens (25 mm×25 mm×16 mm) were cut, then leached for 14 days according to EN 84 before conducting a three month "rot jar test" as specified by the Australasian Wood Preservation Committee (Laboratory Decay Test for Hazard Classes H3, H4 and H5, AWPC, 2007). Untreated controls contained no fungicide. Triadimefon alone displayed a typical dose response when challenged with *Tyromyces palustris* and *Fomitopsis lilacino-gilva* but a flat dose response with *Serpula lacrymans* (a weak point). Cyproconazole alone was more effective than triadimefon and displayed partial inhibition of *Serpula lacrymans* (Table 5).

TABLE 5

Rot jar test results for triadimefon and cyproconazole as glueline fungicides.

| | | Percentage weight loss | | |
|---|---|---|---|---|
| Treatment | gai/m3 | Tyromyces palustris | Fomitopsis lilacino-gilva | Serpula lacrymans |
| Untreated | 0 | 29.9 | 22.6 | 40.5 |
| Triadimefon | 62.5 | 28.7 | 17.8 | 42.4 |
| | 125 | 29.2 | 16.7 | 43.8 |
| | 250 | 16.5 | 10.3 | 42.2 |
| | 500 | 7.6 | 8.2 | 44.9 |
| Cyproconazole | 62.5 | 25.0 | 7.6 | 38.0 |
| | 125 | 16.0 | 4.1 | 38.0 |
| | 250 | 17.1 | 2.7 | 37.9 |
| | 500 | 4.3 | 0.8 | 29.6 |

Example 8

Plywood was manufactured following the procedure in Example 7 using triadimefon and triadimenol as the glueline fungicides and tested by the rot jar method after leaching. The data in Table 6 demonstrates that triadimenol was more efficacious than triadimefon when acting alone in the glueline, consistent with the results obtained on agar plates in Examples 4 and 5.

TABLE 6

Rot jar test results for triadimefon and triadimenol as glueline fungicides.

| | | Percentage weight loss | | |
|---|---|---|---|---|
| Treatment | gai/m3 | Tyromyces palustris | Fomitopsis lilacino-gilva | Antrodia xantha |
| Untreated | | 20.6 | 34.1 | 32.8 |
| Triadimefon | 250 | 14.2 | 19.1 | 29.4 |
| | 500 | 10.7 | 13.8 | 20.3 |
| | 1000 | 2.0 | 5.1 | 12.5 |
| | 2000 | 0.4 | 3.6 | 6.1 |
| Triadimenol | 250 | 9.6 | 9.0 | 24.7 |
| | 500 | 6.5 | 5.1 | 18.4 |
| | 1000 | 0.9 | 1.6 | 11.2 |
| | 2000 | 0.3 | 0.9 | 1.0 |

Example 9

In order to examine the interaction between triadimefon and cyproconazole in the glueline a synergy trial was performed using plywood manufactured with fungicide-supplemented PF resin and the rot jar method described above. Six glueline rates (expressed as gai/m$^3$) of triadimefon alone, cyproconazole alone, triadimefon+cyproconazole (10:1) and triadimefon+cyproconazole (6:1) were used to establish $EC_{50}$ values by regression analysis. Synergy was determined by the Wadley method as described above using the $EC_{50}$ values. Synergy was observed in all but one instance (Table 7).

TABLE 7

Combined action of triadimefon and cyproconazole as glueline fungicides on decay fungi evaluated by the rot jar method.

| Fungicide | $EC_{50}$ (obs) | $EC_{50}$ (exp) | SF |
|---|---|---|---|
| *Antrodia xantha* (brown rot) | | | |
| Triadimefon | 248 | | |
| 10:1 Ratio | 172 | 211 | 1.22 |
| 6:1 Ratio | 252 | 194 | 0.77 |
| Cyproconazole | 84 | | |
| *Fomitopsis lilacino-gilva* (brown rot) | | | |
| Triadimefon | 121 | | |
| 10:1 Ratio | 38 60 | 1.58 | |
| 6:1 Ratio | 36 | 47 | 1.31 |
| Cyproconazole | 10 | | |
| *Serpula lacrymans* (dry rot) | | | |
| Triadimefon | 14328 | | |
| 10:1 Ratio | 2500 | 3863 | 1.55 |
| 6:1 Ratio | 1674 | 2725 | 1.63 |
| Cyproconazole | 465 | | |

Example 10

A similar experiment to that in Example 9 demonstrates synergy in the glueline between triadimefon and cyproconazole at ratios ranging from 20:1 to 6:1 (Table 8).

TABLE 8

Combined action of triadimefon and cyproconazole as glueline fungicides on *Coniophora puteana* evaluated by the rot jar method.

| Fungicide | $EC_{50}$(obs) | $EC_{50}$(exp) | SF |
|---|---|---|---|
| Triadimefon | 2591144 | | |
| 20:1 Ratio | 4094 | 7236 | 1.768 |
| 15:1 Ratio | 1872 | 5516 | 2.947 |
| 10:1 Ratio | 2189 | 3795 | 1.734 |
| 6:1 Ratio | 1368 | 2416 | 1.766 |
| Cyproconazole | 345 | | |

Example 11

Plywood 29 mm thick was manufactured from seven 4.3 mm rotary peeled *Pinus radiata* sapwood veneers using PF resin supplemented with various rates of triadimefon plus cyproconazole at a 10:1 ratio. Plywood was also manufactured using non-supplemented PF resin (untreated), and using PF resin supplemented with the formulation auxiliaries minus active ingredients (solvent control). The finished plywood was then sprayed with the same mixtures to cover the top and bottom faces of the plywood. Test specimens (25 mm×25 mm×29 mm) were cut, leached and tested by the rot jar method as described in Example 7. As a result of the unexpected synergy between triadimefon and cyproconazole the mixture provided excellent dose responses when tested against a wide range of fungi (Table 9), including the dry rot *Serpula lacrymans*, which was not controlled by triadimefon and was only partially controlled by cyproconazole

TABLE 9

Rot jar test results for triadimefon + cyproconazole (10:1) as a glueline fungicide.

| Treatment | Glue line gai/m³ | Surface gai/m² | Percentage weight loss | | | | |
|---|---|---|---|---|---|---|---|
| | | | *Tyromyces palustris* | *Coniophora puteana* | *Fomitopsis lilacino-gilva* | *Antrodia xantha* | *Serpula lacrymans* |
| Untreated | | | 19.2 | 28.1 | 18.0 | 16.3 | 23.0 |
| Solvent control | | | 17.8 | 32.7 | 13.5 | 16.2 | 23.5 |
| Triadimefon + cyproconazole | 450 + 45 | 2.2 + 0.22 | 0.7 | 22.3 | 1.2 | 1.0 | 19.6 |
| | 900 + 90 | 4.4 + 0.44 | 0.6 | 14.5 | 0.4 | 0.4 | 18.9 |
| | 1800 + 180 | 8.8 + 0.88 | 0.4 | 0.6 | 0.4 | 0.0 | 5.0 |
| | 2700 + 270 | 13.2 + 1.32 | 0.5 | 0.8 | 0.4 | 0.0 | 4.4 |

Example 12

In the preceding examples the fungicides were challenged against individual decay fungi in an otherwise sterile environment (autoclaved agar, gamma irradiated rot jar blocks, etc). Next, wood products glueline-treated with the synergistic fungicidal mixture were challenged with an uncontrolled mixture of decay organisms in an accelerated test simulating a real world situation where the wood product is saturated with water and maintained in a warm and moist environment. Sheets of plywood were manufactured as described in Example 11. The sheets were glued together in a cold press with a cold cure phenol-resorcinol-formaldehyde resin supplemented with the 10:1 triadimefon:cyproconazole mixtures and solvent control at the same rates as in the original hot cured gluelines. The final 58 mm thick panels were then sprayed top and bottom with the corresponding products (see Table 10). For comparison untreated 58 mm panels were treated with a light organic solvent preservative (LOSP) containing tebuconazole and propiconazole as specified by ASNZS1604.3 (plywood). The LOSP treatment corresponds to Hazard Class 3 (H3, i.e. exposed to the weather with periodic wetting, in above ground situations). This "Reference Preservative" was applied at the full H3 rate, ½ H3 rate and ¼ H3 rate as stipulated by AWPC, 2007. Specimens were subjected to a bin test for Hazard Class 1.2 (H1.2, protected from the weather, above ground, but with a risk of moisture content conducive to decay) developed by Scion Research, Rotorua, New Zealand. Samples were cut to the dimensions shown in FIG. 1 where the exposed gluelines are the top and bottom faces and the ends. End pieces 100 mm long were cut off and stapled back in place at the joins (1) to enable periodic internal inspection.

The specimens were exposed to a wide range of fungal spores from the air, processing equipment and soak water. As an additional challenge feeder blocks (2) comprising 30 mm×30 mm×7 mm pieces of untreated solid *Pinus radiata* sapwood pre-inoculated with *Antrodia xantha* and *Serpula lacrymans* were positioned with one fungal species at each end. A label (3) was placed between feeder blocks (2) for identification purposes. Ten replicates of each treatment were arranged randomly in stacks with intervening fillets of untreated *Pinus radiata* sapwood and placed in 180 Liter plastic bins. The bins contained enough water to maintain 100% humidity and were sealed and maintained at approximately 25° C. Table 10 shows the averaged data for decay assessments after approximately 18 months. Minimal surface and cross sectional decay was only apparent at the two low rates of the triadimefon+cyproconazole glueline treatment, with the plywood completely intact at the two higher rates. The LOSP comparative data indicates a very high level of performance of the glueline treatment. Although H3 treatments are officially verified by a more challenging test method, the data clearly indicate protection equal to or better than that provided by a H3 Reference Preservative can be provided by low to intermediate rates of the glueline treatment. Moreover, this high level performance was achieved in the presence of the dry rot fungus *Serpula lacrymans* which was not controlled by either triadimefon or cyproconazole alone.

TABLE 10

Results of an H1.2 bin trial for triadimefon + cyproconazole (10:1) as a glueline fungicide.

| Treatment | Glueline gai/m³ | Surface gai/m² | Surface decay coverage (%) | Cross sectional decay (%) |
|---|---|---|---|---|
| Glueline treated plywood | | | 1 ½ years | |
| Untreated | | | 40 | 64 |
| Solvent control | | | 27 | 28 |
| Triadimefon + cyproconazole | 450 + 45 | 2.2 + 0.22 | 1 | 2 |
| | 900 + 90 | 4.4 + 0.44 | 1 | 1 |
| | 1800 + 180 | 8.8 + 0.88 | 0 | 0 |
| | 2700 + 270 | 13.2 + 1.32 | 0 | 0 |
| LOSP treated plywood | | | | |
| Solvent control | | | 19 | 38 |
| Tebuconazole + propiconazole | | ¼ H3 rate | 5 | 8 |
| | | ½ H3 rate | 2 | 5 |
| | | H3 rate | 1 | 1 |

The glueline composition and method of treatment of the invention enabled by the unexpected synergy between triadimefon and cyproconazole is superior to the LOSP treatment, and to other post manufacturing methods of preservation, in that the process for introducing the preservative into the wood product can be incorporated directly into any existing manufacturing process for engineered and reconstituted wood products that uses glue. Other preservation methods require at least one additional process step (the treatment step, often also a re-drying or flashing off step), LOSP methods produce solvent residue problems, and aqueous systems can produce distortion of the wood, etc. Finally use of the synergistic composition produces a very high level of resistance to decay under challenging test conditions.

ADVANTAGES

The present invention has one or more of the following advantages:
Comparatively inexpensive
Reduced toxicity
Easier to use
Safer to use
Maintains integrity of resin component
Maintains final product bond strength
Increased efficacy against dry rots
Increased efficacy against soft rots
Broad spectrum control against fungal pathogens
Improved glueline preservative

EQUIVALENTS CLAUSE

The Invention may also broadly be said to consist in the parts, elements and features referred or indicated in the specification, individually or collectively, and any or all combinations of any of two or more parts, elements, members or features and where specific integers are mentioned herein which have known equivalents such equivalents are deemed to be incorporated herein as if individually set forth.

MODIFICATIONS AND VARIATIONS

The invention has been described with particular reference to certain embodiments thereof. It will be understood that various modifications can be made to the above-mentioned embodiment without departing from the ambit of the invention. The skilled reader will also understand the concept of what is meant by purposive construction.

The examples and the particular proportions set forth are intended to be illustrative only and are thus non-limiting.

Throughout the description and claims of the specification the word "comprise" or variations thereof are not intended to exclude other additives, components, integers or steps.

KIT OF PARTS

It will also be understood that where a product, method or process as herein described or claimed and that is sold incomplete, as individual components, or as a "kit of Parts", that such exploitation will fall within the ambit of the invention.

What we claim is:

1. A method for the preservation of a glued wood product against a broad spectrum of fungi selected from the group of fungi causing brown rot, white rot, dry rot and soft rot, the method comprising the steps of:
   (i) providing at least one of wood flakes, strands, particles, fibres and veneers;
   (ii) providing a glue additive comprising a fungicidally effective amount of:
      (A) a first active ingredient comprising triadimefon, and
      (B) a second active ingredient comprising cyproconazole at synergistic weight ratios of (A) to (B) from 20:1 to 6:1, wherein the glue additive is to be applied at application rates which vary within the range from 100 gai/$m^3$ to 4,490 gai/$m^3$ for triadimefon (A) and within the range from 10 gai/$m^3$ to 2,000 gai/$m^3$ for cyproconazole (B), provided that the total application rate does not exceed 4,500 gai/$m^3$;

(iii) providing a glue to bond the at least one of wood flakes, strands, particles, fibres and veneers;

(iv) configuring the at least one of wood flakes, strands, particles, fibres and veneers, the glue additive, and the glue; and (v) forming the glued wood product.

2. The method of claim 1 comprising an additional step (vi), wherein the glue additive is applied as a surface treatment for the formed glued wood product.

3. The method of claim 1 wherein the application rate for triadimefon (A) is from 100 gai/$m^3$ to 2,700 gai/$m^3$ and the application rate for cyproconazole (B) is from 100 gai/$m^3$ to about 300 gai/$m^3$.

4. The method according to claim 1 wherein the glue additive is applied during manufacture of a glued wood product by direct application to at least one of wood flakes, strands, particles, fibres and veneers at any stage prior to the addition of the glue component; or by mixing into the glue prior to a veneer layup operation; or by mixing the glue additive with at least one of wood flakes, strands, particles, and fibres by injection into a refiner, blow line, or tumbler prior to, at the same time or after injection of the glue mixture.

5. The method according to claim 1 wherein the glued wood product is selected from:

(i) an engineered wood product comprising glued wood veneers, such products including laminated veneer lumber and plywood;

(ii) a reconstituted wood product selected from the group comprising at least one of glued wood flakes, strands, particles and fibres, such products including strand board, oriented strand board, parallel strand lumber, flake board, particle board, medium density fibreboard, high density fibreboard, hardboard, wood plastic composites, and mixtures thereof; and (iii) a product comprising engineered and reconstituted wood products.

6. The method according to claim 1 wherein the glue component of the glued wood product is selected from an amino resin including urea-formaldehyde, melamineformaldehyde, melamine-urea-formaldehyde, and hydroxymethyl or alkoxymethyl derivatives of urea, melamine, benzoguanamine, or glycoluril, a phenolic resin including phenol-formaldehyde, resorcinol-formaldehyde or phenol-resorcinol-formaldehyde, an isocyanate resin, a PYA adhesive, a polyurethane adhesive, a protein based adhesive, and/or a derivative or combination thereof.

7. A preserved glued wood product treated by the method of claim 1.

8. The method according to claim 1, wherein the synergistic weight ratios of (A) to (B) from 20:1 to about 10:1.

9. The method according to claim 2, wherein the glue additive has a synergy factor of 1.96 or greater based on an $ED_{90}$ for the triadimefon and the cyproconazole.

* * * * *